(12) United States Patent
Ashdown et al.

(10) Patent No.: US 11,606,914 B2
(45) Date of Patent: Mar. 21, 2023

(54) FIBER-OPTIC SHEET LIGHTING

(71) Applicant: Suntracker Technologies Ltd., Victoria (CA)

(72) Inventors: Ian Edward Ashdown, West Vancouver (CA); Wallace Jay Scott, Victoria (CA)

(*) Notice: Subject to any disclaimer, the term of this patent is extended or adjusted under 35 U.S.C. 154(b) by 6 days.

(21) Appl. No.: 17/824,810

(22) Filed: May 25, 2022

(65) Prior Publication Data

US 2022/0287247 A1  Sep. 15, 2022

Related U.S. Application Data

(63) Continuation-in-part of application No. 17/690,683, filed on Mar. 9, 2022, now Pat. No. 11,382,280, which is a continuation of application No. 17/314,858, filed on May 7, 2021, now Pat. No. 11,310,964, which is a continuation-in-part of application No. 17/177,579, filed on Feb. 17, 2021, now Pat. No. 11,122,747, which is a continuation of application No. 16/981,596, filed as application No. PCT/CA2019/050359 on Mar. 22, 2019, now Pat. No. 10,966,376.

(60) Provisional application No. 63/193,333, filed on May 26, 2021, provisional application No. 62/660,911, filed on Apr. 20, 2018, provisional application No. 62/647,650, filed on Mar. 24, 2018.

(51) Int. Cl.
*A01G 7/04* (2006.01)
*F21V 23/00* (2015.01)
*G02B 5/02* (2006.01)
*F21V 8/00* (2006.01)

(52) U.S. Cl.
CPC ............ *A01G 7/045* (2013.01); *F21V 23/003* (2013.01); *G02B 5/0252* (2013.01); *G02B 6/0006* (2013.01)

(58) Field of Classification Search
CPC ....................................................... G02B 6/001
See application file for complete search history.

(56) References Cited

U.S. PATENT DOCUMENTS

| | | | |
|---|---|---|---|
| 8,975,605 B2 | 3/2015 | Neister | |
| 9,700,642 B2 | 7/2017 | Neister | |
| 10,322,297 B1 | 6/2019 | Hinds et al. | |
| 2004/0037091 A1 | 2/2004 | Guy | |
| 2005/0231973 A1* | 10/2005 | Cassarly | G02B 6/001 362/551 |
| 2013/0048877 A1* | 2/2013 | Thoren | B08B 17/02 250/492.1 |

(Continued)

*Primary Examiner* — Andrew J Coughlin

(57) ABSTRACT

Laser light is coupled to optical fibers arranged in a sheet, which may be in the form of netting, mesh or fabric. Scattering centers or bends in the optical fibers allow the coupled light to escape from the sides of the fibers. Depending on the selection of wavelengths for the lasers, the resulting luminous sheet may be used for illumination of crops grown in vertical farms. The laser wavelengths excite plant photopigments for predetermined physiological responses, and the light source intensities may be temporally modulated to maximize photosynthesis and control photomorphogenesis responses. Each laser may be independently controlled, and at least one laser may emit ultraviolet-C radiation. The luminous sheet may be used for purification of air flowing through an air duct.

22 Claims, 6 Drawing Sheets

(56) References Cited

U.S. PATENT DOCUMENTS

| | | | |
|---|---|---|---|
| 2015/0075384 A1* | 3/2015 | Park | B01D 53/885 96/224 |
| 2018/0236113 A1* | 8/2018 | Gross | A61L 2/26 |
| 2019/0099613 A1 | 4/2019 | Estes et al. | |
| 2021/0187318 A1 | 6/2021 | Hinds et al. | |
| 2021/0220666 A1 | 7/2021 | Zapol et al. | |

* cited by examiner

FIBER-OPTIC SHEET LIGHTING

TECHNICAL FIELD

The subject matter of the present invention relates to a system of providing optical radiation to plants grown in controlled environments or to purify air by killing microbial organisms. More specifically, it relates to providing diffused laser light of particular wavelengths that is delivered by optic fibers.

BACKGROUND

It is becoming increasingly economical to grow plants in controlled environments such as greenhouses and plant factories. In these environments, horticultural luminaires are typically mounted above the planting beds, although inter-row lighting is sometimes used for trellised plants such as vine tomatoes.

Before the introduction of light-emitting diode (LED) technology, horticultural luminaires typically used fluorescent or high-pressure sodium (HPS) lamps to provide sufficient optical radiation ("light") for the plants to perform photosynthesis while growing. In addition, incandescent lamps were sometimes used to advance or delay flowering in plants such as poinsettia. Regardless of the technology, the lamp spectral power distribution (SPD) and photosynthetic photon flux (PPF) emitted by the lamps were fixed parameters.

The first generation of LED-based horticultural luminaires employed blue and red LEDs whose narrow-band spectral emissions were chosen to match the spectral absorption peaks of chlorophyll A and B (FIG. 1), the reasoning being that this would result in the most efficient use of the photon flux for plant photosynthesis. It was also helpful in that the absorption peaks of approximately 450 nm (blue) and 660 nm (red) coincided with the peak efficacies of industry-standard InGaN and AlInGaP inorganic LED technologies (FIG. 4).

Some manufacturers now offer second-generation horticultural luminaires with LED peak wavelengths ranging from 400 nm (blue) to 750 nm (far-red), including broadband "white" light from phosphor-coated LEDs. A few horticultural luminaire manufacturers further include ultraviolet LEDs in their products, including UV-B (280 nm to 315 nm) and UV-A (315 nm to 400 nm), while others offer different fixed SPDs designed to promote vegetative growth or flowering.

Recent horticultural research has shown, however, that plants have a much more complex relationship with the spectral power distribution of incident optical radiation than has previously been recognized. In addition to photosynthesis, the spectral power distribution also influences photomorphogenesis, phototropism, shade avoidance, secondary metabolite production, pest resistance, circadian rhythm entrainment, and more.

Recent horticultural research has also shown that the spatial and temporal distribution of optical radiation has significant influence on plant growth and health. Inter-row lighting is an example of spatial distribution, where horizontally-oriented optical radiation incident on the leaves of closely-spacing trellised vine tomatoes has been shown to improve yield and fruit quality. Similarly, varying the daily photoperiod during the growth cycle is an example of temporal distribution, where shortening the photoperiod from 16 hours to 12 hours during flowering has been shown to influence the production of tetrahydrocannabinolic acid (THCa) in *Cannabis sativa* crops.

Unfortunately, prior art horticultural luminaires do not provide the means of precisely controlling the spectral power, spatial and temporal distributions of optical radiation needed to realize the benefits of improved plant growth and health in controlled environments as evidenced by this recent research.

Prior art horticultural luminaires have until recently consisted of either HPS or metal halide (MH) arc lamps with rotationally symmetric reflectors and refractive optics, or linear fluorescent lamps with reflectors and diffusers. Arc lamps produce large amounts of infrared radiation and conductive heat, and so the luminaires must typically be positioned at least several meters above the plant canopy in greenhouses and vertical farms to avoid overheating the plant leaves and flowers. It is difficult to control the spatial intensity distribution of the photosynthetic photon flux, and so the luminaires are typically arranged in a grid pattern simply to provide spatially even photosynthetic photon flux density (PPFD) on the plant canopy from overhead. HPS and MH lamps are further limited in that they cannot be dimmed, and their spectral power distributions are fixed.

Linear fluorescent lamps do not produce significant amount of infrared radiation or conductive heat, and so can be positioned within centimeters of the plant canopy. However, each lamp can produce only a limited amount of photosynthetic photon flux, making them unsuitable for use in greenhouses where PPFD levels comparable to daylight are typically required. Their spectral power distributions are also fixed, and their linear form factor makes it difficult to control their spatial intensity distributions.

Linear horticultural luminaires with high-flux LEDs are commercially available, such as the Arize Lynk™ from Current by GE, that provide blue and red semiconductor LEDs in combination with phosphor-coated white light LEDs. Their spectral power distributions, however, are fixed, and they do not provide collimation optics to achieve spatial intensity distributions substantially different from that of linear fluorescent lamps.

Prior to their discontinuation as legal products, incandescent lamps were used to control flowering of ornamental plants such as poinsettia. Edison-base LED lamps such as the Ariz™ Greenhouse Pro from Current by GE are available to fulfill this role, but their form factor makes it difficult to control their spatial intensity distributions, and their spectral power distributions are fixed.

Some commercially-available horticultural luminaires provide a choice of vegetative ("veg") or flowering ("bloom") spectral power distributions, and are capable of being dimmed remotely, such as for example the TopLight™ luminaire and associated smartPAR™ control software from LumiGrow (Emeryville, Calif.).

LED-based horticultural luminaires designed specifically for research and development are available, such as for example the PHYTOFY RL™ from OSRAM (Munich, Germany). This particular product includes an array of five different quasimonochromatic LEDs with nominal peak wavelengths at 385 nm (ultraviolet-A), 450 nm (blue), 521 nm (green), 660 nm (red), and 735 nm (far-red), as well as phosphor-coated white light LEDs with a correlated color temperature of 2700K. The LEDs are controlled by six independent pulse-width modulation (PWM) drivers, each with a dimming range of 10 to 100 percent, which enables researchers to generate a variety of spectral power distributions and PPFD levels on the plant canopy that can be varied by software executed on a remote computer and communicating with the drivers through a network interface.

There are a number of disadvantages to such horticultural luminaires. First, each high-flux LED is mounted in its own package and affixed to a common heat sink. This makes it difficult to control the spatial intensity distribution of the luminaire. Second, the LEDs cannot be arranged in a linear array without large variations in spectral power distribution along the length of the luminaire. Assuming for example a 2.0 centimeter spacing between LED packages, the six LEDs would span 12 centimeters and require a distance of at least five times (i.e., 60 centimeters) to ensure an approximately constant spectral power distribution on the plant canopy.

A third disadvantage is that each LED package must be electrically and thermally connected to a large and expensive metal-core circuit board to provide electrical power and extract the generated heat using passive or actively-cooled heat sinks. Active cooling using electrically-powered fans is a particular problem in greenhouses, where the luminaire housings are typically subjected to high humidity, dripping water, and possibly water-jet washing.

Even with active cooling, the maximum photosynthetic photon flux that can be generated by an LED-based horticultural luminaire is limited by the ability of the cooling system to extract conductive heat from the LED packages. Water cooling is an option, but this involves water supply and return lines that must be routed between each luminaire and a central pump and heat exchanger.

A fourth disadvantage is that semiconductor LED manufacturers cannot precisely control the peak wavelengths of their products, and so must "bin" LED die with similar wavelengths during the packaging process. The smaller the range of acceptable peak wavelengths within each bin, the lower the production yield and the higher the product cost.

This is significant in that the absorption spectra of plant photopigments typically exhibit narrow distributions. For example, the spectral absorption of chlorophyll A in FIG. 1 has a full-width half-maximum (FWHM) value of only 15 nm at 660 nm, while chlorophyll B similarly has a FWHM value of 15 nm at 435 nm. For comparison, LUXEON Rebel™ color LEDs as manufactured by Lumileds (San Jose, Calif.) are binned in 5 nm increments for blue (e.g., 440 nm to 445 nm), but 10 nm increments for red (e.g., 650 nm to 660 nm). Botanical studies such as Johkan, M., et al. 2012. "Effects of Green Light Wavelength and Intensity on Photomorphogenesis and Photosynthesis in *Lactuca sativa*," Environmental and Experimental Botany 75:128-133, have shown that differences in peak wavelength as small as 10 nm can have marked deleterious effects on the growth and health of plants grown in controlled environments.

A fifth disadvantage is that even with multiple independently-controlled LED drivers, the spectral power distribution is limited to a combination of the emissions from quasimonochromatic LEDs with fixed center wavelengths and broadband phosphor-coated LEDs with fixed SPDs. Recent research has shown that different plant species respond to combinations of different wavelengths. The "Emerson effect" is a well-known example, where the addition of red light has been shown to increase the efficacy of photosynthesis in plants exposed to broadband (400 nm to 700 nm) optical radiation. More recent studies have shown that varying the ratio of red to blue light influences vegetative growth and flowering, adding green light to white light tends to promote photosynthetic activity, varying the ratio of red to far-red light triggers seed germination and advances or delays flowering, ultraviolet radiation promotes the production of flavonoids and other secondary metabolites while limiting vegetative growth and increasing resistance to pests and fungal infections, and more.

FIG. 1 shows the spectral absorptances in vitro of chlorophyll A and B, while FIG. 2 shows the spectral absorptances of the $P_r$ and $P_{fr}$ isoforms of phytochrome and FIG. 3 shows the spectral absorptances of UV RESISTANCE LOCUS 8 (UVR8) and beta-carotene. Common to all of these photopigments are markedly rapid changes in spectral absorptance with wavelength, emphasizing the need to "tune" the peak wavelengths of narrowband LEDs or monochromatic lasers to excite these pigments with maximum efficacy. For example, irradiating UVR8 with 295 nm ultraviolet-B radiation is only 50 percent as effective as irradiation with 280 nm radiation.

These photopigments are further only the most well-known and studied for their involvement in photosynthesis (chlorophylls A and B and beta-carotene), photomorphogenesis (phytochrome), and UVR8 (ultraviolet radiation protection). Other plant photopigments include cryptochromes (involved in circadian and circannual rhythms), other carotenes (photosynthesis), xanthophylls (light energy modulation and photosynthesis), anthocyanins (nutrient recovery and pollination attractants), and phototropins (phototropism). Altogether, there are hundreds of known plant photopigments, many with as-yet-unknown functions. More importantly, the Emerson effects and other physiological responses to different spectral power distributions show that there are likely many as-yet undiscovered interactions between plant pigments and their effect on plant health and growth.

SUMMARY OF INVENTION

The inventors have recognized a need for a horticultural luminaire that provides improved control over the spectrum that is used to illuminate the plants, and that narrowband optical radiation, and monochromatic radiation from laser sources in particular, offer the best opportunities to limiting crosstalk between plant photopigments, both when studying their interactions and also in growing plants in controlled environments.

A linear array of optical elements is optically coupled via fiber optic cables to one or more laser light sources, and are housed within a hollow linear optic with a holographic diffuser. Laser wavelengths are chosen to maximally excite plant photopigments for predetermined physiological responses, and the light source intensities may be temporally modulated to maximize photosynthesis and control photomorphogenesis responses.

Disclosed herein is a horticultural lighting assembly comprising: one or more optical components mounted on a substrate and each optically coupled to at least one optical fiber that delivers laser radiation to the optical component; and a linear or elliptical holographic diffuser located to diffuse light emanating from said optical components.

Also disclosed herein is a horticultural lighting system comprising: one or more optical components mounted on a substrate; at least one optical fiber coupled to each optical component; a linear or elliptical holographic diffuser located to diffuse light emanating from said optical components; and one or more laser light modules optically coupled to said optical fibers.

Further disclosed herein is a method for inducing a predetermined physiological response in a plant comprising; (a) determining wavelengths suitable to excite photopigments in the plant to cause the predetermined physiological response; (b) providing a horticultural lighting system having a lighting assembly comprising: one or more optical components mounted on a substrate; at least one optical fiber coupled to each optical component; and a linear or elliptical holographic diffuser located to diffuse light emanating from said optical components; and also having one or more laser light modules optically coupled to said optical fibers, wherein each laser light module generates composite monochromatic optical radiation with the wavelengths, the wavelengths being within a range of 200 nm to 3000 nm; (c) locating the lighting assembly to illuminate the plant; and (d) driving lasers in the laser light modules to generate the composite monochromatic optical radiation.

Still further disclosed is a horticultural lighting system comprising: one or more optical components mounted on a substrate; at least one optical fiber coupled to each optical component; a linear or elliptical holographic diffuser located to diffuse light emanating from said optical components; and one or more laser light modules optically coupled to said optical fibers. Each laser light module comprises: a laser light source that produces a laser beam; a diffractive optic beam splitter located to split the laser beam into multiple beams; a beam collimator located to collimate the multiple beams; a dual-band dichroic mirror located to combine each of the multiple beams with one of further multiple beams provided by a further laser light source, further diffractive optic beam splitter and further beam collimator, to result in multiple combined beams; and a fiber optic assembly into which the multiple combined beams are coupled, wherein said optical fibers in part form a portion of the fiber optic assembly. At least one of the one or more laser light modules generates optical radiation with a wavelength in the range of 200 nm to 280 nm.

Also disclosed is a method for inducing a predetermined physiological response in a plant comprising: (a) determining wavelengths suitable in the plant to cause the predetermined physiological response; (b) providing a horticultural lighting system comprising a lighting assembly having one or more optical components mounted on a substrate, at least one optical fiber coupled to each optical component, and a linear or elliptical holographic diffuser located to diffuse light emanating from said optical components, and one or more laser light modules optically coupled to said optical fibers, wherein each laser light module generates composite monochromatic optical radiation with the wavelengths, the wavelengths being within a range of 200 nm to 3000 nm; (c) locating the lighting assembly to illuminate the plant; and (d) driving lasers in the laser light modules to generate the composite monochromatic optical radiation.

Also disclosed is a lighting system comprising: a sheet comprising one or more optical fibers, each optical fiber having a section that is side-emitting; and one or more laser light sources optically coupled to the one or more optical fibers; wherein the one or more laser light sources generate optical radiation with one or more monochromatic wavelengths in the range of 200 nm to 3000 nm.

DETAILED DESCRIPTION

Glossary

Composite monochromatic radiation—Polychromatic radiation made up of multiple monochromatic or narrow-band spectra, such as, for example, the combined light produced by two different types of laser.

LED—Light-emitting diode

Monochromatic radiation—radiation made up of a single, narrow-band spectrum, such as, for example, the light produced by a laser.

PPFD—Photosynthetic photon flux density

Sheet—this is to be understood as a perforated sheet, a non-perforated sheet, a piece of netting, a piece of mesh or any other structure that is generally planar and flexible with or without holes that are several times larger than the thickness of the structure.

SPD—Spectral power distribution

System

Figure 1:
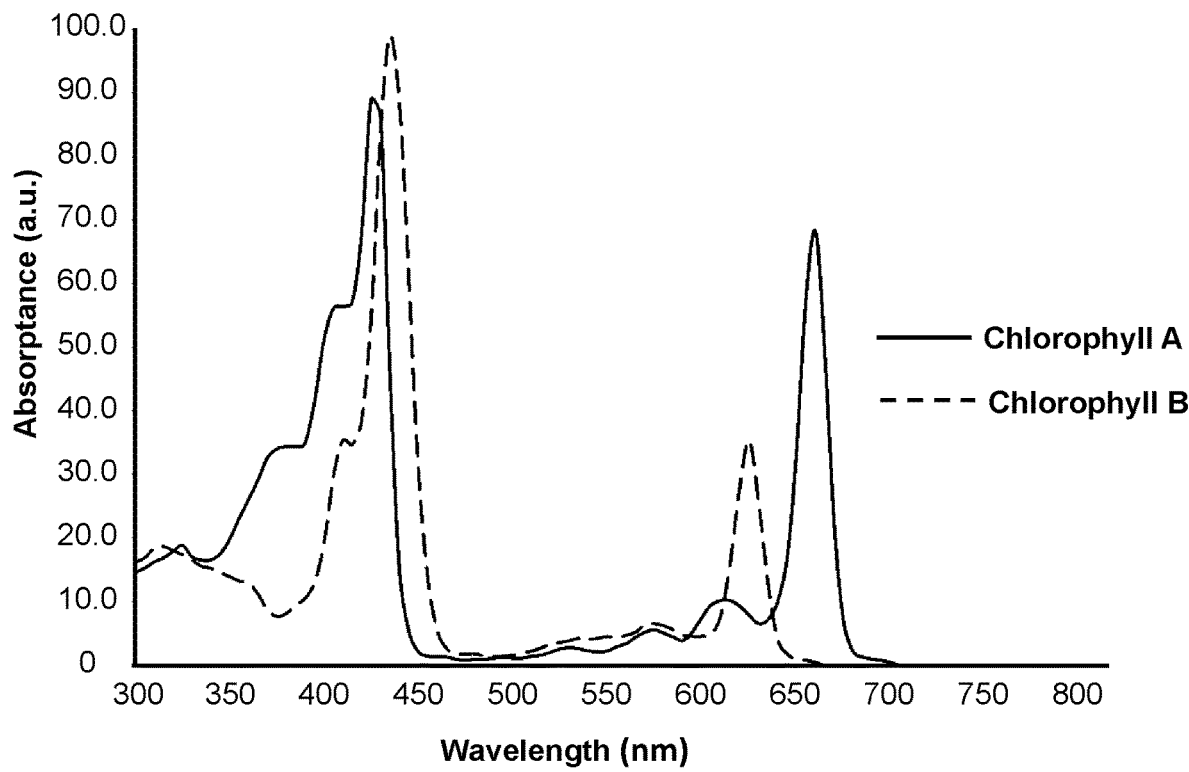
FIG. 1 shows the spectral absorptances of chlorophyll photopigments.
Figure 2:
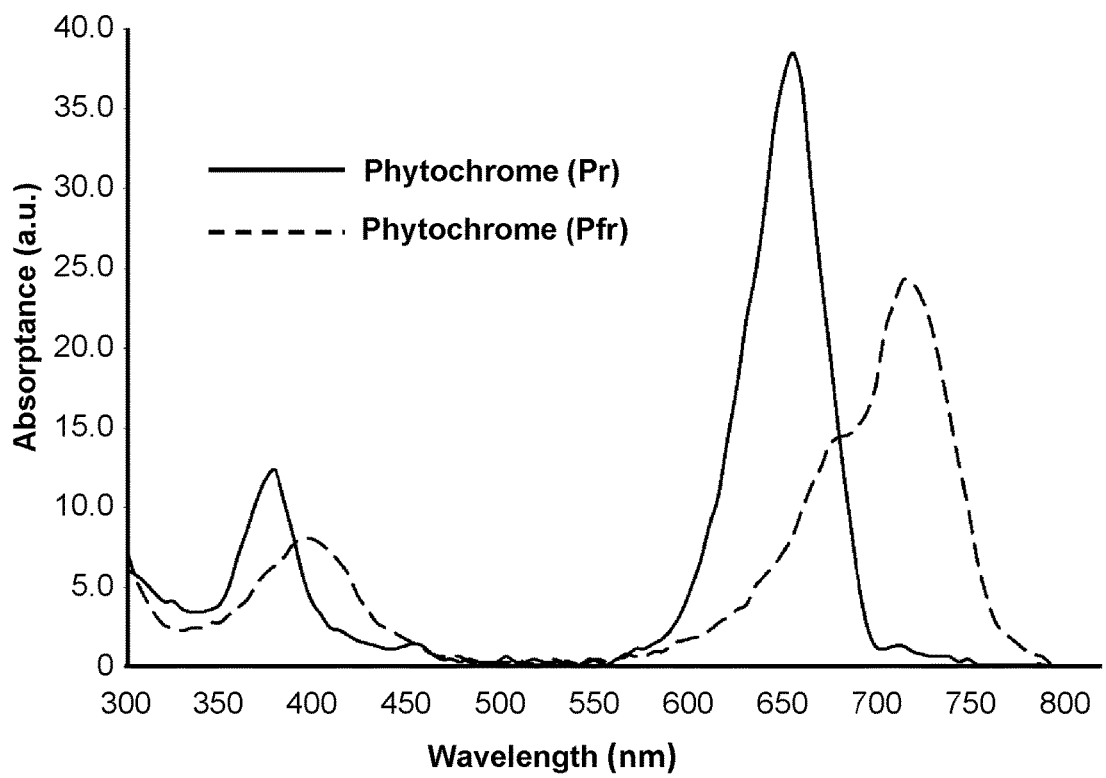
FIG. 2 shows the spectral absorptances of phytochrome photopigments.
Figure 3:
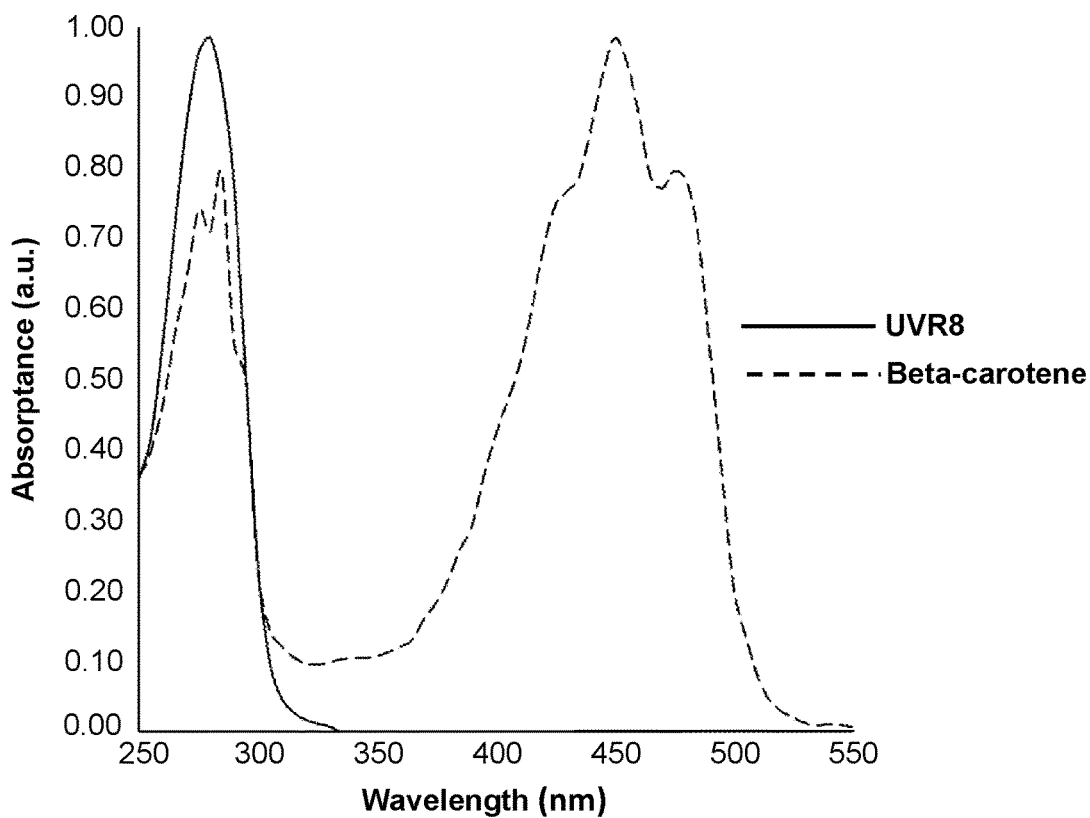
FIG. 3 shows the spectral absorptances of beta-carotene and UVR8 photopigments.
Figure 4:
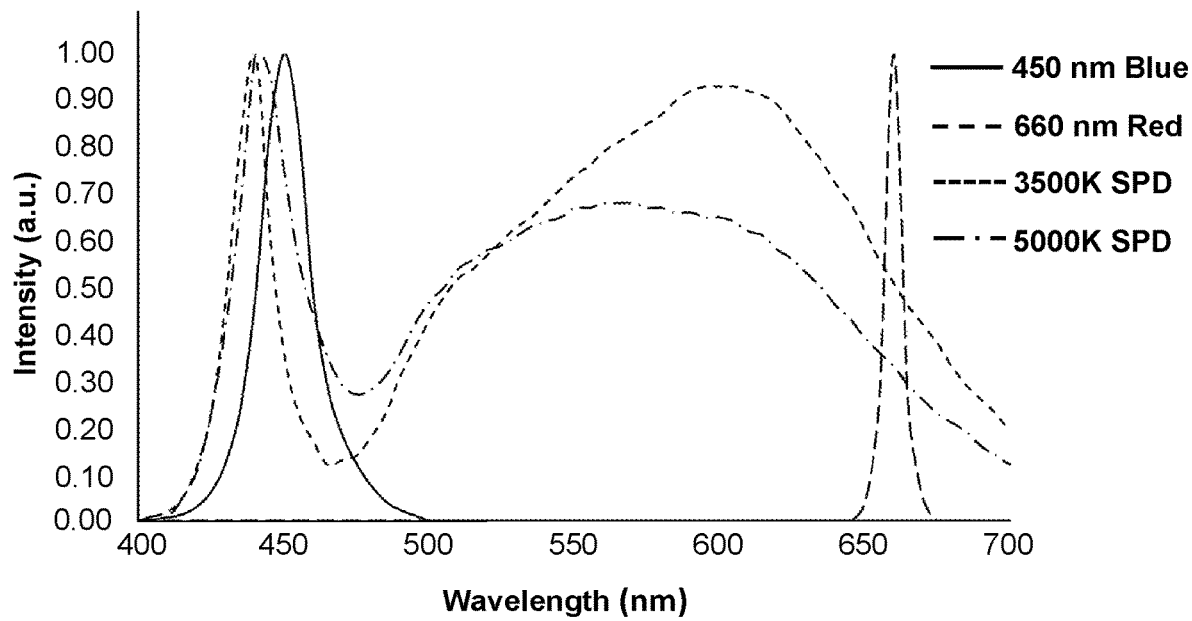
FIG. 4 shows the spectral power distributions of various semiconductor LEDs.
Figure 5:
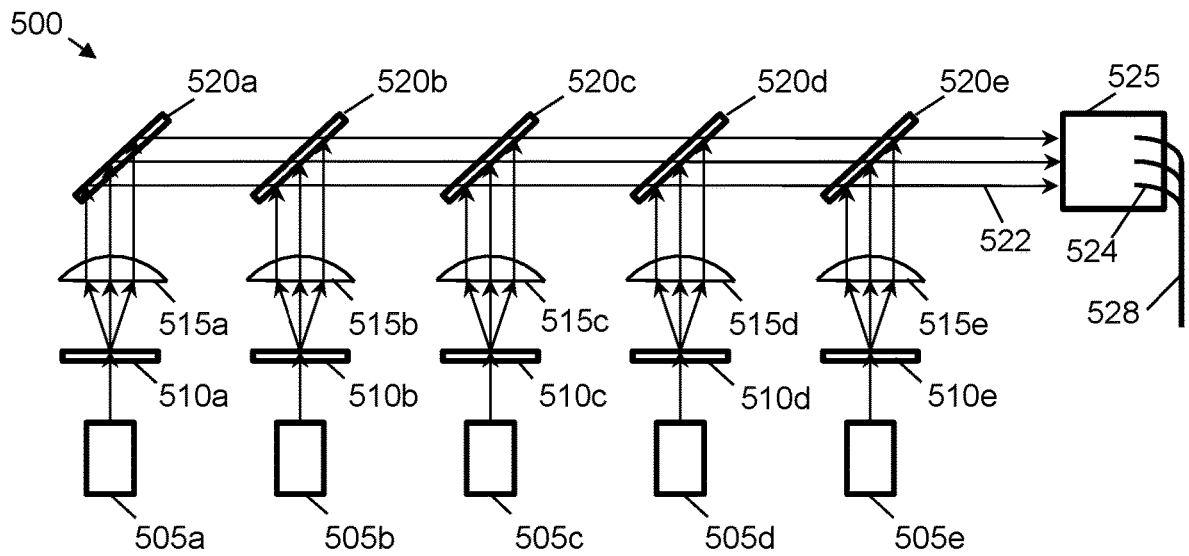
FIG. 5 shows an embodiment of a laser light module, according to an embodiment of the present invention.

FIG. 5 shows a laser module 500 that has one or more laser light sources 505a-e, each of which emits monochromatic radiation with a different wavelength. This radiation is received by a diffractive optic beam splitter 510a-e (e.g., Golub, M. A. "Laser Beam Splitting by Diffractive Optics," Optics & Photonics News, February 2004, pp. 36-41), that splits the incident beam into two or more diffraction orders. These divergent beams are then collimated by a refractive or diffractive optical element 515a-e and incident upon a mirror 520a or dual-band dichroic mirror 520b-e that reflects the monochromatic radiation while passing other wavelengths. The result is that individual divergent beams from each of the diffractive optic beam splitters 510a-e are combined to form a combined beam 522. Each combined beam 522 includes radiation from each of the laser light sources 505a-e. Each combined beam 522 is then received by an optical fiber 524 in fiber optic assembly 525. The optic fibers 524 form a bundle 528 for delivering the composite monochromatic radiation.

It is currently assumed that the wavelength range of photobiologically active radiation for plants is 280 nm to 800 nm. However, medical studies such as, for example, Karu, T. I. 2008, "Mitochondrial Signaling in Mammalian Cells Activated by Red and Near-IR,", Photochemistry and Photobiology 84(5):1091-1099, indicate that cytochrome c oxidase (CCO), a protein complex present in the mitochondria of mammalian cells that have a spectral absorption peak at approximately 820 nm, increase adenosine triphosphate (ATP) production when irradiated by near-infrared radiation. These studies have been used to explain the benefits of photobiomodulation using near-infrared lasers or LEDs, an alternative medicine for humans and animals. However, CCO is an essential component of the respiration of all eukaryotic cells, including plants, as shown for example by Dahan, J. et al. 2014. "Disruption of the CYTOCHROME C OXIDASE DEFICIENT1 Gene Leads to Cytochrome c Oxidase Depletion and Reorchestrated Respiratory Metabolism in *Arabidopsis*," Plant Physiology 166:1788-1802. (Other mechanisms have also been proposed, as reviewed in, for example, de Freitas, L. F. et al. 2016, "Proposed Mechanisms of Photobiomodulation of Low-Light Level Therapy," IEEE Journal of Selected Topics in Quantum Electronics 22(3):7000417.) Plants in general may therefore benefit from, and indeed require, near-infrared radiation for optimum growth and health. Such radiation may be generated, for example, by gallium arsenide (GaAs), aluminum gallium arsenide (AlGaAs), gallium antimonide (GaSb), or gallium indium arsenide antimonide (GaInAsSb) semiconductor LEDs or laser diodes. The wavelengths of the laser light sources 505a-e may therefore include any wavelength in the range of 280 nm to 3000 nm.

Figure 6:
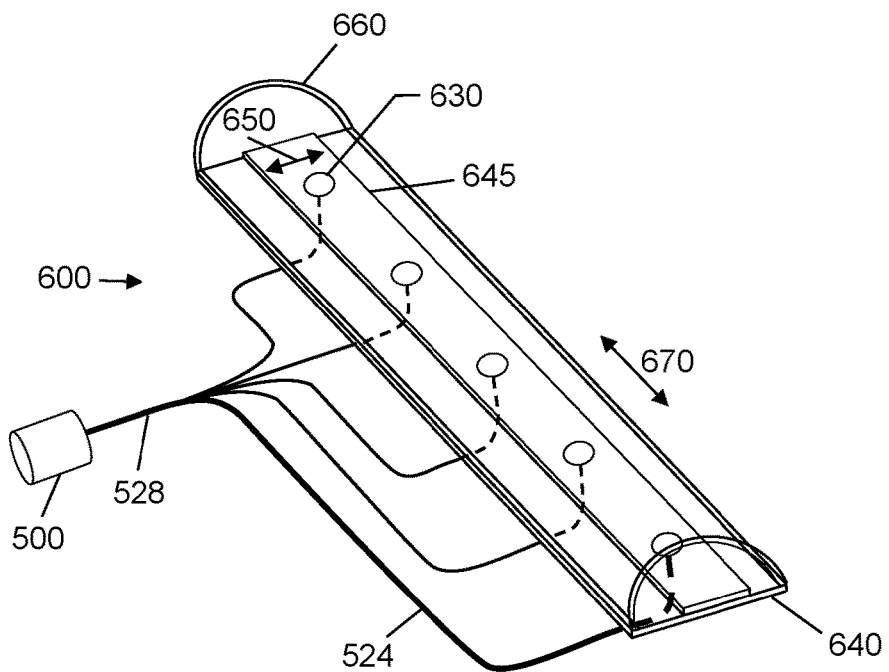
FIG. 6 shows an embodiment of the horticultural lighting assembly with a linear array of fiber optics optically coupled to one or more laser light sources, according to an embodiment of the present invention.

FIG. 6 shows a horticultural lighting assembly 600 (or luminaire). The lighting assembly 600 is optically coupled to one or more laser modules 500 via optical fiber bundle 528, which includes one or more optical fibers 524, wherein the laser modules 500 are located either within the luminaire housing or at a remote location. If at a remote location, it is easier to dissipate the heat generated by the lasers and reduce its influence on the plants. One or more optical components 630 are mounted on a substrate 640 and optically coupled to the optical fibers 524. The optical components 630 distribute the composite monochromatic radiation transmitted by the optical fibers 524 in a desired angular distribution.

In one embodiment, optical components 630 include diffusers that optionally include an inorganic or organic luminophore, such as for example an yttrium-aluminum-garnet (YAG) phosphor or a fluorescent dye, to absorb a portion of the composite monochromatic radiation coupled from optical fibers 524 and emit a broadband optical wavelength range.

As used herein, "phosphor" refers to any material that shifts the wavelengths of light irradiating it and/or that is fluorescent and/or phosphorescent, and is utilized interchangeably with the term "light-conversion material." As used herein, a "phosphor" may refer to only the powder or particles or to the powder or particles with the binder. The specific components and/or formulation of the phosphor and/or binder material are not limitations of the present invention. The binder may also be referred to as an encapsulant or a matrix material. A "luminophore" is an atom or functional group in a chemical compound that is responsible for its luminescent properties.

Figure 7:
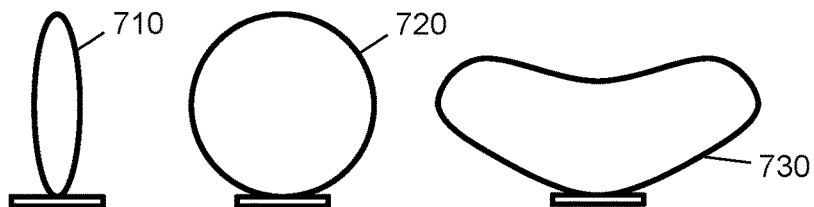
FIG. 7 shows different angular diffusion distributions from linear or elliptical holographic diffusers.

In another embodiment, optical components 630 include a holographic diffuser or are located below a holographic diffuser 645 (e.g., U.S. Pat. No. 7,255,458, System and Method for the Diffusion of Illumination Produced by Discrete Light Sources) with a linear or elliptical diffusion pattern that is oriented in direction 650. The angular diffusion in direction 650 may exhibit different patterns. As shown in FIG. 7, these patterns may include a narrow beam distribution 710, a broad cosine distribution 720, or a batwing distribution 730.

Referring again to FIG. 6, the optical radiation emitted from optical components 630 is incident upon another holographic diffuser 660, which has a linear or elliptical diffusion pattern that is oriented in direction 670, orthogonal to direction 650. In one embodiment, the holographic diffuser 660 is formed into a hemicylinder that is mechanically connected to substrate 640. Similar to optical components 630 that include holographic diffusers or are located below a holographic diffuser 645, holographic diffuser 660 may exhibit, as shown in FIG. 7 a narrow beam distribution 710, a broad cosine distribution 720, or a batwing distribution 730.

The holographic diffuser 660 serves an entirely different function to the apparatus disclosed in U.S. Pat. No. 7,255,458. The purpose of the prior art invention is to generate the visual appearance of the discrete LEDs as a linear line source, whereas the present invention uses the diffusion of optical radiation from holographic diffuser 660 (and optionally in combination with optical components 630 when including holographic diffusers, or in combination with holographic diffuser 645) to produce a constant PPFD at a reasonably close distance from the luminaire along its length, rather than "hot spots" created by the optical components 630 that act as discrete emitters.

A specific, non-limiting example of the lasers and phosphors in a laser module 500 for a horticultural lighting assembly 600 includes an InGaN blue-violet laser diode with a wavelength selected from the range of 400 nm to 410 nm, an InGaN blue laser diode with a wavelength selected from the range of 445 nm to 465 nm, an InGaN green laser diode with a wavelength selected from the range of 510 nm to 540 nm, an AlInGaP red laser diode with a wavelength selected from the range of 650 nm to 670 nm, an AlGaAs far-red laser diode with a wavelength selected from the range of 720 nm to 750 nm, and one or more phosphors such as, for example, cerium-doped yttrium aluminum garnet (Cr:YAG) or europium/dysprosium-doped strontium aluminate (Eu,Dy:SrAl$_2$O$_4$).

Figure 8:
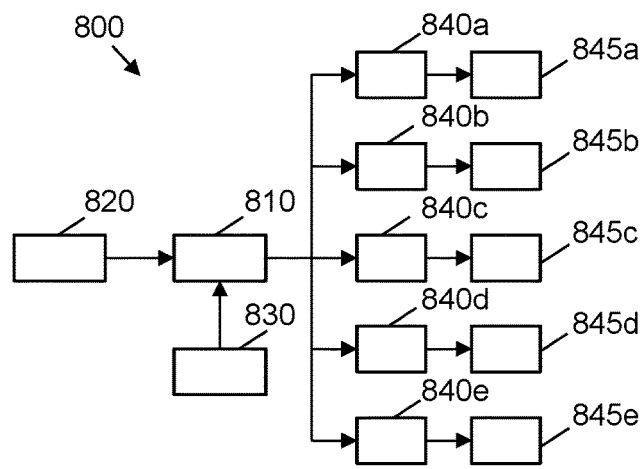
FIG. 8 shows a block diagram of a control system for the horticultural lighting system, according to an embodiment of the present invention.

The radiant flux emitted by laser light sources 505a-e of FIG. 5 may be individually modulated to achieve a composite monochromatic spectral power distribution as delivered to fiber optic assembly 525. In an embodiment of the control system 800 of the horticultural lighting system, shown in FIG. 8, one or more laser light sources 845a-e are electrically connected to laser drivers 840a-e, which may temporally modulate the radiant flux of each of the laser light sources by means of, for example, digital pulse width modulation or analog current control. Each driver 840a-e is electrically connected to controller 810, which may receive input signals from one or more sensors 820, including for example optical radiation sensors, daylight photosensors or pyranometers, temperature sensors, and relative humidity sensors, and also from timer 830.

As reported by Kanechi, M. et al. 2016. "Effects of Pulsed Lighting Bases Light-emitting Diodes on the Growth and Photosynthesis of Lettuce Leaves," Acta Horticulturae 1134, photosynthetically active radiation (PAR) modulated at a rate of microseconds to milliseconds improves the photosynthesis efficency. Also, as reported by Shimada, A. et al. 2011. "Red and Blue Pulse Timing Control for Pulse Width Modulation Light Dimming of Light Emitting Diodes for Plant Cultivation," Journal of Photochemistry and Photobiology B-Biology, 104:399-404, the phase difference between pulses of different colors may either increase or decrease the rate of plant growth.

The radiant flux emitted by laser light sources 845*a-e* (and 505*a-e* of FIG. 5) is therefore modulated in some embodiments at a rate of microseconds to milliseconds, wherein the modulation phase and frequency of each wavelength may be independently varied.

As reported by Harun, A. et al. 2013. "Red and Blue LED with Pulse Lighting Control Treatment for *Brassica Chinensis* in Indoor Farming," Proc. 2013 IEEE Conference on Open Systems, pp. 231-236, pulses of one hour of light followed by 15 minutes of darkness more than tripled the rate of photosynthesis. The radiant flux emitted by laser light sources 845*a-e* (and 505*a-e* of FIG. 5) is therefore modulated in some embodiments at a rate of seconds to minutes to simulate "sun flecks," brief occurrences in solar irradiance that occur in forest understories when sunlight is able to directly reach the ground.

Method

Figure 9:
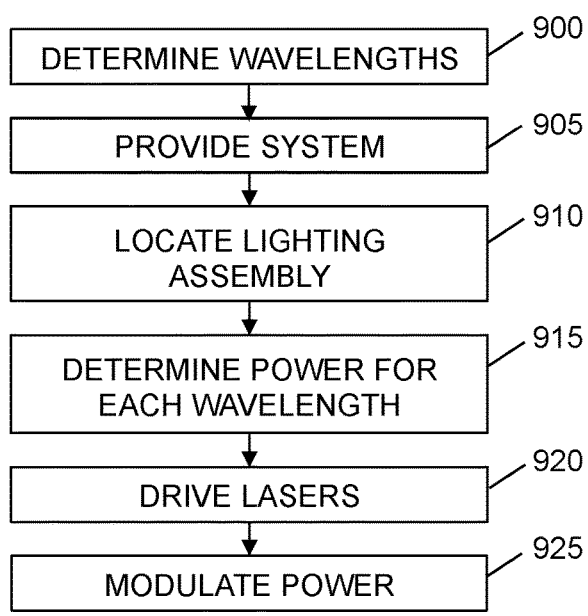
FIG. 9 shows a flowchart for use of the horticultural lighting system, according to an embodiment of the present invention.

Referring to FIG. 9, an exemplary method is shown for use of a horticultural lighting system incorporating the laser module 500 and the horticultural lighting assembly 600. In step 900, the wavelengths desired for the particular plant are determined. In step 905, the system is provided with a laser module that can provide the determined wavelengths. In step 910, the horticultural luminaire assembly 600 is located to illuminate the plants from a desired position and direction. In step 915, the desired output powers of each of the lasers in the laser module 500 is determined. In step 920, the laser module is switched on to drive the lasers, illuminating the plants with the desired spectrum and power density. Optionally, the lasers are collectively modulated in step 925 by dimming them temporarily by 10-100% for periods ranging from a timescale of microseconds to minutes.

Figure 10:
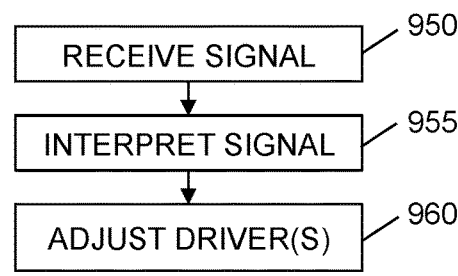
FIG. 10 is a flowchart of operation of the control system, according to an embodiment of the present invention.

FIG. 10 shows control steps taken by the control system 800. In step 950, the controller 810 receives a signal from one of the sensors 820 or from the timer 830. In step 955, the controller 810 interprets the signal by comparing it, for example, to a threshold, or by otherwise analyzing it. In step 960, the controller 810 adjusts the power to at least one of the laser drivers 840*a-e* in order to modify the output of the corresponding laser light sources 845*a-e*.

Figure 11:
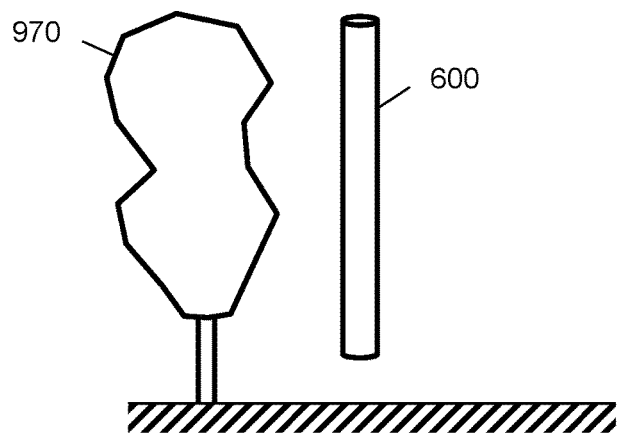
FIG. 11 shows a horticultural lighting assembly mounted vertically as inter-row lighting.

In an embodiment shown in FIG. 11, the horticultural lighting assembly 600 is oriented vertically and located in proximity to and beside one or more plants 970. In this configuration, the lighting system serves as, for example, inter-row lighting.

Figure 12:
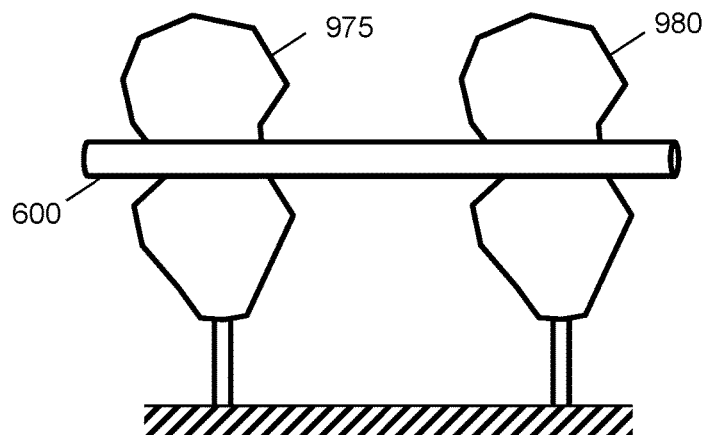
FIG. 12 shows a horticultural lighting assembly mounted horizontally as inter-row lighting.

In an embodiment shown in FIG. 12, the horticultural lighting assembly 600 is oriented horizontally and located in proximity to and beside one or more plants, 975, 980. In this configuration, the lighting system serves as, for example, inter-row lighting.

Figure 13:
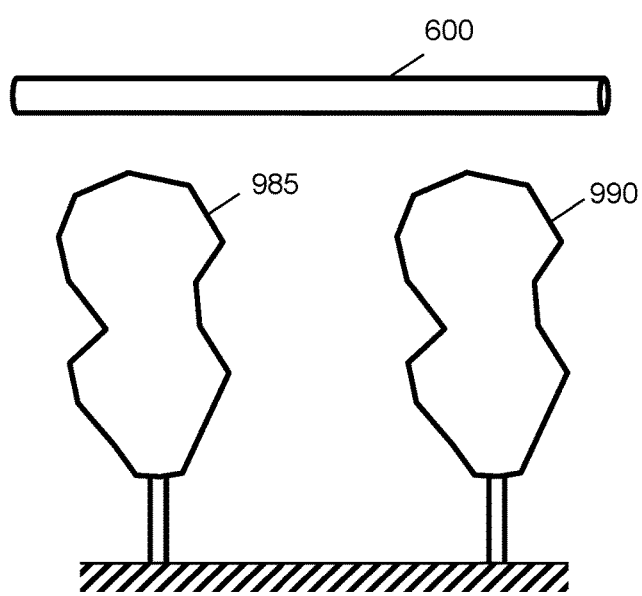
FIG. 13 shows a horticultural lighting assembly mounted horizontally as overhead lighting.

In an embodiment shown in FIG. 13, the horticultural lighting assembly 600 is oriented horizontally and located in proximity to and above one or more plants, 985, 990. In this configuration, the lighting system serves as, for example, overhead lighting.

Ultraviolet-C

In addition to UV-A and UV-B, the use of UV-C in horticulture has added benefits to the grower. UV-C is defined as 200 nm to 280 nm. Of these ultraviolet ranges, UV-C has the strongest germicidal effect (referred to as Ultra Violet Germicidal Irradiation or UVGI) and has been widely used in the form of mercury lamps to inactivate microorganisms. UVGI is a means to combat, for example, Sphaerotheca macular (powdery mildew), Botyrtis *cinerea* (bud mold, or gray mold), and other types of DNA-based molds and bacteria that plague growing plant life, including *Cannabis* plants. UV-C can also be used in upper air ducts to help clean the greenhouse, plant factory, or vertical garden facility.

In addition to the UVGI effects, at appropriate dosage rates UV-C light can have other effects on plants that are beneficial to growers. For example, UV-C may be used to increase branching on some plant species. This effect avoids the need to pinch plants and to apply plant growth regulators. Delayed flowering is also obvious on some UV-C treated plants (see for example Bridgen, M. P. (2016). Using ultraviolet-C (UV-C) irradiation on greenhouse ornamental plants for growth regulation. Acta Hortic. 1134, 49-56).

However, the degrading effect of UV-C on many materials, including plastics commonly seen in greenhouses, means that widespread use of UV-C light may result in higher replacement costs to growers. In addition, there are known health risks associated with high dose exposure to UV-C to humans and the environment. As a result, control of the light emitted by these devices is critical, as systems that result in high doses and exposure such as mercury lamps or even LEDs may be problematic.

The effectiveness of any UVGI source is based on the dose received, rather than mere exposure (see for example: Ashdown, Ian. Designing an Ultraviolet-C Disinfection System, allthingslighting.org, 9 Jun. 2020). By providing diffused laser light of particular wavelengths that is delivered by optic fibers, the dose can be increased over the area in which the optic fibres are located, obviating the need for higher radiation from traditional sources to ensure sufficient dose.

With recent advances in technology, deep-ultraviolet laser diodes with wavelengths selected from the range of 200 nm to 280 nm have become available. In addition, fibre optics have recently come available for certain wavelengths of UV-C (see for example Newport Corporation's model 78252 and others). Such advances have made it possible to employ these technologies as contemplated by the system disclosed herein to provide diffused laser light of 200 nm to 280 nm wavelength that is delivered by optic fibers.

Referring back to FIGS. 5 and 6, a specific, non-limiting example of a laser in a laser module 500 for a horticultural lighting assembly 600 includes an AlGaN deep-ultraviolet laser diode with a wavelength selected from the range of 200 nm to 280 nm. The wavelengths of the laser light sources 505*a-e* may therefore include any wavelength in the range of 200 nm to 3000 nm.

Further Systems

The advantage of lasers is that near-perfect optical coupling of the radiation into the fiber can be achieved; the challenge is in extracting the radiation from the fiber with minimal loss. Some optic fibers are side-emitting rather than end-emitting, and are designed to purposely leak light through their sides. This may be achieved by maintaining bends in the optic fibers, adding scattering centers to the fiber core or increasing the refractive index of the cladding, for example. Furthermore, the jacket around the cladding may act as a diffuser. By weaving such side-emitting optic fibers into a sheet, with non-emitting support fibers or other structure, a luminous sheet can be made.

Figure 14:
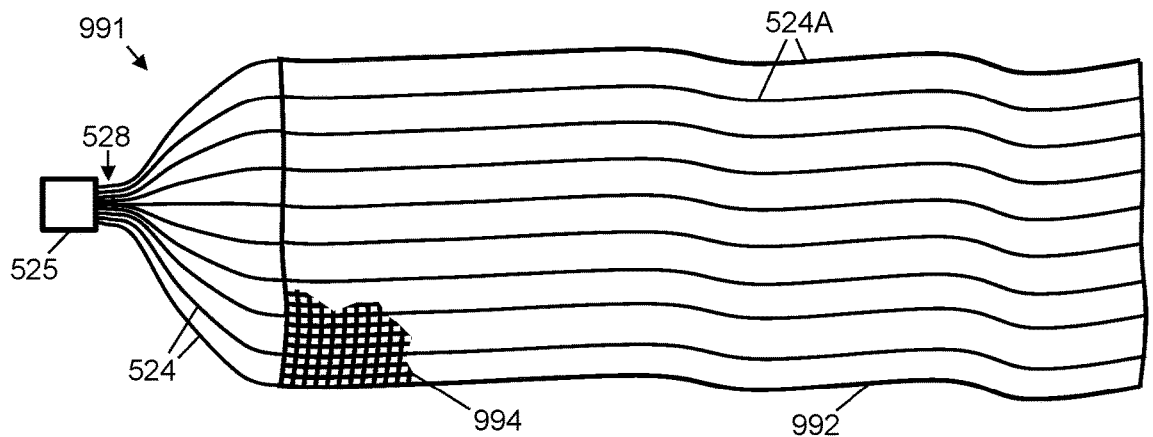
FIG. 14 shows a horticultural lighting assembly, according to an embodiment of the present invention.

FIG. 14 shows a horticultural lighting assembly 991 or luminaire that incorporates an optic fiber sheet 992. Here, "sheet" is to be understood as a perforated sheet, a non-perforated sheet, a piece of netting, a piece of mesh or any other structure that is generally planar and flexible with or without holes that are several times larger than the thickness of the structure. The lighting assembly 991 is optically coupled to a fiber optic assembly 525 via optical fiber bundle 528, which includes one or more optical fibers 524. Laser light is directed to the fiber optic assembly 525 as explained above. The optic fiber sheet 992 includes portions 524A of the optic fibers 524 that are made to be side-emitting. The portions 524A of the optic fibers 524 are woven into or otherwise attached to the structure 994 of the sheet, which may be a net or a mesh, for example. In some embodiments the sheet may include a material or fabric. For a fabric, the thread count is unimportant, so a practical fiber optic textile for horticultural applications may be much more loosely woven than a fabric used for garments, for example. However, it would still be possible to use more finely woven fabrics. In some embodiments a fabric is not used, but instead a sheet of perforated plastic is used, which may be flexible.

Depending on the wavelength(s) of the laser light coupled to the optical fibers 524, the fibers of the fabric sheet may be selected to be those that will suffer less photo-degradation compared to other materials. For example, polyester fabric may be used for UV laser light. The threads of the fabric may be translucent, allowing the light emitted from the optic fibers to pass through, and may act as diffusers of the light. In some embodiments, the threads may be reflective at the wavelength(s) of the lasers. Likewise, the material used for a perforated sheet may be selected for a particular resistance to photo-degradation, translucency or reflectivity.

In some embodiments, the optic fibers may be all or the majority of fibers in the sheet that run in one direction, with only non-optic threads running in the perpendicular direction. In other embodiments, the optic fibers run in both perpendicular directions. In some embodiments, the optic fibers are woven into the fabric or attached to the sheet in a wave pattern or loop pattern. This is so that in those regions the fibers always have a curvature above a minimum threshold level, which allows the laser light to escape from the sides of the fibers. In some embodiments, the optic fibers are woven into the sheet with a curvature that gradually increases from the input end of the optic fiber to the other end. In some embodiments, the scattering centers in the optic fibers are non-uniformly spaced or gradually increasing density per unit area of the sheet moving away from the light-input end of the sheet. This is in order to provide a more uniform light output from the sheet than if the scattering centers were equally spaced or evenly distributed throughout. In some embodiments, the optical fibers are arranged in the sheet or scattering features within the optical fibers are located to provide a uniform light output per unit area of the sheet over a majority of the sheet (i.e. more than half).

In some embodiments, the sheets include stiffeners or reinforcements in order to prevent the sheet from being folded or overly curved, which may break the optic fibers woven into it or attached to it. The stiffeners may be, for example, wires made from spring steel, thin carbon-fiber rods or fiberglass. While adding stiffness, the optic-fiber sheet is still flexible enough to be rolled up for storage and transport. If the optic fibers run in only one direction in the sheet, then the stiffeners run parallel to that direction, and are not necessary in the direction that is perpendicular to the direction of the optic fibers.

The optic fiber sheet 992 may emit laser light from its surfaces in the range of 200 nm to 3000 nm, depending on the wavelength of the lasers used to supply the fiber optic assembly 525. In some embodiments, laser light may be fed into more than one edge of the optic fiber sheet 992.

In other embodiments, the dichroic mirrors may not be required, as each optic fiber may carry only one wavelength of light, and optic fibers carrying similar wavelengths may be spread out in the optic fiber textile or sheet with optic fibers carrying other wavelengths in between.

Figure 15:
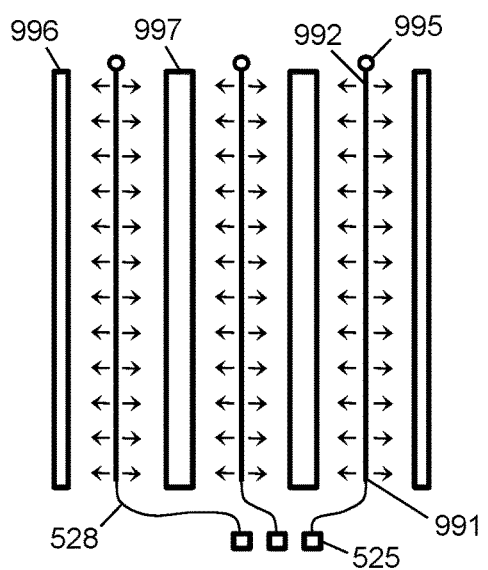
FIG. 15 shows a horticultural lighting assembly for a vertical farm, according to an embodiment of the present invention.

FIG. 15 shows an arrangement of luminaires 991 with optic fiber sheets 992 used for illuminating vertical farms. The luminaires 991 are hung on rails 995, for example, and placed between vertical growth substrates 996, 997, which provide support, water and nutrients to the plants. In other embodiments, other supporting techniques may be used to maintain the luminaires in place. For example, they may be suspended from hooks or cables. Some or all of the vertical substrates 996, 997 and the intervening luminaires may be translatable laterally in order to temporarily provide increased access to the crops.

In some embodiments, the luminaires 991 are fastened down to the floor or other fixing points at their bottom edges in order to maintain a fixed distance from the growth substrates 996, 997, which may be necessary where there is air movement in the vertical farm. In some embodiments, the luminaires 991 are weighted at their bottom edges for the same reason. In some embodiments, there are physical spacing rods or cables between the growth substrates 996, 997 and the luminaires 991, which maintain a fixed spacing between the luminaires and the growth substrates.

Figure 16:
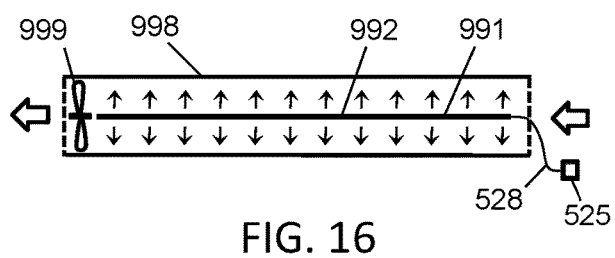
FIG. 16 shows an air duct for purifying air, according to an embodiment of the present invention.

FIG. 16 shows an air duct 998 with a fan 999 that draws air through the air duct. The air duct is located in a room, greenhouse or vertical farm, for example. Inside the air duct 998, the optic fiber sheet 992 of a luminaire 991 is supported so that it irradiates the air that passes through the duct. The sheet 992 may be supported by a rigid frame or grid, for example, or it may be suspended by cables. In other cases, the luminaire 991 may have enough rigidity to be supported by its edges on ledges or in grooves on the inner walls of the air duct. Shields may be present around the openings of the air duct if necessary to prevent light from leaving the air duct. In one embodiment, UV-C light is used to purify the air, while not exposing occupants of the room in which it is installed to dangerous levels of UV-C. In this example, the optic fibers in the textile or sheet may be quartz fibers, for example.

It is evident that other arrangements may be used in different embodiments of the air duct 998. For example, the mesh of the optic fiber sheet 992 may be coarse enough for the air to pass through from one side to another at a sufficient rate to maintain a safe environment in the room. In this case, the air may be directed to pass through one or more layers of the sheet 992. To achieve this, for example, a single sheet may be mounted in a rippled configuration and the air directed through each wave of the ripples. In some embodiments, the air duct is mounted outside the room, for example, above a false ceiling. Multiple fans may be used instead of one.

In some embodiments, the optic fiber sheet 992 may emit light from both of its sides, a side of the sheet being one of the two largest surfaces of the sheet. In some embodiments, the sheet may emit light from only one of its sides. In other embodiments, the sheet may emit light from one or more of its edges. Where light is emitted from both sides of the sheet, each side may emit a different light intensity and/or spectral composition, the emission from each side being controlled on a separate channel. In other embodiments, the light emitted from both sides is controlled on the same channel. Where light is emitted from an edge or edges of the sheet, this edge-emitted light may be controlled differently to the light emitted from one or both of the sides of the sheet. In other embodiments, when the same channel is used for light emitted from both sides of the sheet, the light emitted from an edge or edges of the sheet may be controlled on this same channel. Depending on the embodiment, the sheet 992 therefore emits the optical radiation from one or more areas of emission selected from a first side of the sheet, a second side of the sheet and one or more edges of the sheet, and each area of emission is controlled via its own channel or via a channel used to control another of said areas of emission.

Figure 17:
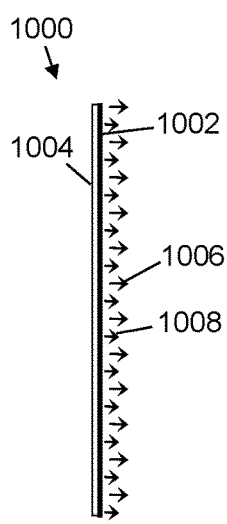
FIG. 17 shows a composite optic fiber sheet, according to an embodiment of the present invention.

In some embodiments and referring to FIG. 17, the optic fiber sheet is a composite sheet 1000, in that it has multiple layers. For example, one layer 1002 may be a light-emitting layer, and another layer may a reflective layer 1004, such as aluminized polyester. In this embodiment, the light emitting layer may emit light on both sides or predominantly on one side, and the reflective sheet may be applied to the non-emitting side or lesser-emitting side of the sheet. The light-emitting layer may be bonded to the reflective layer, for example, or other techniques may be used to fasten the two layers together. The reflective layer serves to reflect light or stray light from the light-emitting layer so that the composite sheet emits light from only one side, as a combination of directly emitted light 1006 and reflected light 1008. The reflective layer 1004 therefore reflects a portion of the optical radiation that is both emitted by the light-emitting layer 1002 and incident upon the reflective layer. At least some or substantially all of the reflected light then passes through the light-emitting layer to be emitted by the sheet 1000.

Figure 18:
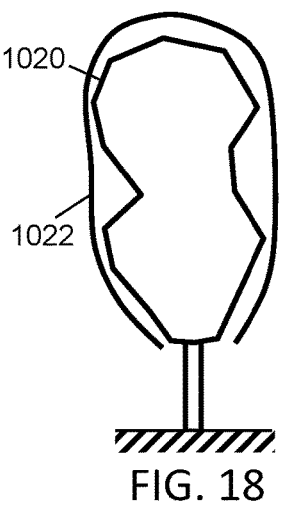
FIG. 18 shows a luminaire wrapped around a plant, according to an embodiment of the present invention.

In some embodiments, the sheet 992 may be wrapped around one or more plants, or anything else that it may be desirable to irradiate. This includes plant trays, furniture, and other items. For example, it may be wrapped around a part of animal or person, or around an enclosure or frame around the animal or person, subject to veterinarian or medical recommendation. An advantage of wrapping the sheet, whether fully or partially, is the potential for an increased dose of light, or a more efficient delivery of the dose. Another advantage may derive from the close proximity of the luminaire to the target for irradiation, which can lead to more efficient use of space. Referring to FIG. 18, the canopy of a plant 1020 is wrapped with a light-emitting sheet 1022.

Throughout the description, specific details have been set forth in order to provide a more thorough understanding of the invention. However, the invention may be practiced without these particulars. In other instances, well known elements have not been shown or described in detail and repetitions of steps and features have been omitted to avoid unnecessarily obscuring the invention. Accordingly, the specification is to be regarded in an illustrative, rather than a restrictive, sense.

It will be clear to one having skill in the art that further variations to the specific details disclosed herein can be made, resulting in other embodiments that are within the scope of the invention disclosed. Two or more steps in the flowcharts may be performed in a different order, other steps may be added, or one or more may be removed without altering the main function of the invention. All parameters, and configurations described herein are examples only and actual choices of such depend on the specific embodiment. For example, different numbers of components may be used; diffusers may be spaced differently relative to each other and to the optical elements; or each combined beam may be fed into multiple optic fibers. Accordingly, the scope of the invention is to be construed in accordance with the substance defined by the following claims.

We claim:

1. A lighting system comprising:
a sheet comprising multiple optical fibers, each optical fiber having a section that is side-emitting;
one or more laser light sources optically coupled to the multiple optical fibers; and
for each of the one or more laser light sources:
a diffractive optic beam splitter located to split a laser beam from the laser light source into multiple beams;
a beam collimator located to collimate the multiple beams; and
a fiber optic assembly into which the multiple collimated beams are coupled, wherein the multiple optical fibers in part form a portion of the fiber optic assembly, wherein each of the multiple collimated beams is coupled into a different one of the multiple optical fibers;
wherein the one or more laser light sources generate optical radiation with one or more monochromatic wavelengths in the range of 200 nm to 3000 nm.

2. The lighting system of claim 1, wherein:
at least one of the multiple optical fibers comprises quartz; and
at least one of the one or more laser light sources generates optical radiation in the range of 200 nm to 280 nm.

3. The lighting system of claim 1, wherein each optical fiber carries a single monochromatic wavelength of optical radiation.

4. The lighting system of claim 1, wherein the multiple optical fibers are woven into the sheet.

5. The lighting system of claim 1, wherein the sheet is a netting, a mesh or is perforated.

6. The lighting system of claim 1, comprising one or more stiffeners in the sheet.

7. The lighting system of claim 1, wherein the multiple optical fibers are arranged in the sheet or scattering features within the multiple optical fibers are located to provide a uniform light output per unit area of the sheet over a majority of the sheet.

8. The lighting system of claim 1 in which there are multiple laser light sources, the system comprising at least one dual-band dichroic mirror located to combine each of the multiple collimated beams from one of the multiple laser light sources with one of the multiple collimated beams from another of the multiple laser light sources.

9. The lighting system of claim 1, further comprising two vertical growth substrates, wherein the sheet is located in a vertical plane between the two vertical growth substrates.

10. The lighting system of claim 9, wherein:
at least one of the multiple optical fibers comprises quartz; and
at least one of the one or more laser light sources generates optical radiation in the range of 200 nm to 280 nm.

11. The lighting system of claim 1, further comprising an air duct and a fan, wherein the sheet is located inside the air duct and the fan is located to move air through the air duct and through or over the sheet.

12. The lighting system of claim 11, wherein:
at least one of the multiple optical fibers comprises quartz; and
at least one of the one or more laser light sources generates optical radiation in the range of 200 nm to 280 nm.

13. The lighting system of claim 1 in which there are multiple laser light sources, the system comprising, for each of the multiple laser light sources, a laser driver that temporally modulates a radiant flux of a laser beam emitted by the laser light source, wherein a modulation phase and a modulation frequency of each laser beam are independently controlled.

14. The lighting system of claim 1 in which there are multiple laser light sources and the multiple laser light sources include:
an InGaN blue-violet laser diode with a wavelength selected from the range of 400 nm to 410 nm;
an InGaN blue laser diode with a wavelength selected from the range of 445 nm to 465 nm;
an InGaN green laser diode with a wavelength selected from the range of 510 nm to 540 nm;
an AlInGaP red laser diode with a wavelength selected from the range of 650 nm to 670 nm; and
an AlGaAs far-red laser diode with a wavelength selected from the range of 720 nm to 750 nm.

15. The lighting system of claim 1 wherein at least one of the one or more laser light sources includes an AlGaN deep-ultraviolet laser diode with a wavelength selected from the range of 200 nm to 280 nm.

16. The lighting system of claim 1, wherein the sheet comprises a reflective layer that reflects a portion of the optical radiation that is incident upon the reflective layer.

17. The lighting system of claim 1, wherein the sheet emits the optical radiation from only one side of the sheet.

18. The lighting system of claim 1, wherein the sheet emits the optical radiation from both sides of the sheet.

19. The lighting system of claim 1, wherein the sheet emits the optical radiation from one or more areas of emission selected from a first side of the sheet, a second side of the sheet and one or more edges of the sheet, and each area of emission is controlled via its own channel or via a channel used to control another of said areas of emission.

20. A lighting system comprising:
a sheet comprising one or more optical fibers, each optical fiber having a section that is side-emitting; and
multiple laser light sources optically coupled to the one or more optical fibers;
wherein the multiple laser light sources generate optical radiation with one or more monochromatic wavelengths in the range of 200 nm to 3000 nm and the multiple laser light sources include:
an InGaN blue-violet laser diode with a wavelength selected from the range of 400 nm to 410 nm;
an InGaN blue laser diode with a wavelength selected from the range of 445 nm to 465 nm;
an InGaN green laser diode with a wavelength selected from the range of 510 nm to 540 nm;
an AlInGaP red laser diode with a wavelength selected from the range of 650 nm to 670 nm; and
an AlGaAs far-red laser diode with a wavelength selected from the range of 720 nm to 750 nm.

21. The lighting system of claim 20, wherein:
at least one of the one or more optical fibers comprises quartz; and
at least one of the multiple laser light sources generates optical radiation in the range of 200 nm to 280 nm.

22. The lighting system of claim 20 wherein at least one of the multiple laser light sources includes an AlGaN deep-ultraviolet laser diode with a wavelength selected from the range of 200 nm to 280 nm.

* * * * *